United States Patent
Hadden

(10) Patent No.: US 8,628,501 B2
(45) Date of Patent: Jan. 14, 2014

(54) SYRINGE STERILIZATION CAP

(76) Inventor: Gordon Hadden, Sarasota, FL (US)

( * ) Notice: Subject to any disclaimer, the term of this patent is extended or adjusted under 35 U.S.C. 154(b) by 0 days.

(21) Appl. No.: 13/332,819

(22) Filed: Dec. 21, 2011

(65) Prior Publication Data

US 2013/0164189 A1    Jun. 27, 2013

(51) Int. Cl.
- *A61M 5/32* (2006.01)
- *A61M 5/14* (2006.01)
- *A61L 2/00* (2006.01)
- *A61L 9/00* (2006.01)
- *A47K 7/02* (2006.01)
- *A47L 13/46* (2006.01)
- *B43L 21/00* (2006.01)

(52) U.S. Cl.
USPC ........... 604/199; 604/256; 422/292; 422/300; 15/244.1

(58) Field of Classification Search
USPC ........... 422/300, 292; 604/256, 199; 15/244.1
See application file for complete search history.

(56) References Cited

U.S. PATENT DOCUMENTS

| | | | |
|---|---|---|---|
| 1,798,188 A * | 3/1931 | Brown | 15/244.1 |
| 2,677,373 A | 5/1952 | Barradas | |
| 3,559,645 A | 2/1971 | Schaller | |
| 3,890,971 A | 6/1975 | Leeson et al. | |
| 4,240,427 A | 12/1980 | Akhavi | |
| 4,273,123 A | 6/1981 | Lemelson | |
| 4,728,321 A | 3/1988 | Chen | |
| 4,874,384 A | 10/1989 | Nunez | |
| 4,883,470 A | 11/1989 | Haindl | |
| 5,000,742 A | 3/1991 | Morrison | |
| 5,026,345 A | 6/1991 | Teringo | |
| 5,125,415 A | 6/1992 | Bell | |
| 5,242,421 A | 9/1993 | Chan | |
| 5,527,283 A | 6/1996 | Swisher, III | |
| 5,807,352 A | 9/1998 | Tamaro | |
| RE39,107 E | 5/2006 | Shaw | |
| 7,887,516 B2 | 2/2011 | Young | |
| 2004/0039341 A1* | 2/2004 | Ranalletta | 604/199 |
| 2007/0113861 A1 | 5/2007 | Knudsen et al. | |
| 2010/0000040 A1* | 1/2010 | Shaw et al. | 15/244.1 |
| 2010/0047123 A1 | 2/2010 | Solomon | |
| 2011/0030726 A1 | 2/2011 | Vaillancourt | |
| 2011/0054440 A1* | 3/2011 | Lewis | 604/506 |
| 2011/0232020 A1 | 9/2011 | Rogers | |
| 2012/0022469 A1 | 1/2012 | Alpert | |

* cited by examiner

*Primary Examiner* — Regina M Yoo

(74) *Attorney, Agent, or Firm* — Charles J. Prescott, P.A.

(57) ABSTRACT

A sterilization cap carried on a needle support end of a syringe. The cap includes a main body having first and second ends, the first end being connectable to the needle support end, as well as being connectable onto the needle support end alone of a primary or IV extension line. A sponge secured within a sponge cavity within the second end is saturated with a sterilizing liquid. A removable cover attached to the second sealingly encloses the sponge until the syringe is used. The second end is sized, when the cover is removed, to fit over a tip of a CLAVE needleless connector extension or IV tubing a distance sufficient to compress the sponge to sterilize the tip with sterilizing liquid expressed from the sponge.

3 Claims, 9 Drawing Sheets

SYRINGE STERILIZATION CAP

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to the field of medical devices, and more particularly to a sterilization cap for a hypodermic syringe which greatly facilitates the sterilization of components either connectable to or associated with the use of a syringe in a medical setting.

2. Description of Related Art

During medical procedures when various IV procedures are in use, all of the needle and/or needleless IV connections made during such procedures, beginning with prepackaged IV and tubular extension components, must be sterilized. The typical procedure for sterilization of such needleless IV connections is through the use of a prepackaged antiseptic swab containing a sterilization liquid such as isopropyl alcohol and/or chlorhexidine glutamate. These antiseptic liquid-saturated swabs are rubbed onto the connector ends of the needless IV connections prior to making those connections with mating IV components. Having to tear open individual swab packs and then awkwardly manually fold and rub the swab around the needleless connections is awkward at best and, on occasion, may be incomplete or missed altogether, leading to a less than ideal sterile environment for various IV installations.

A number of prior U.S. patents are directed toward protecting the needle attached to a syringe, but do not appear to have a direct bearing on the uniqueness and patentability of the present invention. In U.S. Pat. No. 7,887,516, a safety cap for medical needles is disclosed which protects against accidental post-use needle sticks. U.S. Pat. No. 4,883,470 teaches a safety cap which is also intended to reduce the likelihood of needle sticks and to facilitate protection and disposal of syringe needles.

A needle safety guard is disclosed in U.S. Pat. No. 4,874,384 teaching a medical needle guard having a pair of telescoping tubular sleeves mountable onto the hub of needles which protect the needle from accidental sticks. In U.S. Pat. No. 4,273,123, a syringe and needle cover is disclosed which receives and retains needles after being broken off or removed from the syringe.

A non-mechanical incapacitation syringe safety needle guard is disclosed in U.S. Pat. No. 5,026,345 which prevents reuse of a syringe and needle assembly and prevents accidental needle injury. In U.S. Pat. No. 4,728,321, a syringe cap with an adhesive holding plug is mountable onto the syringe for encasing the needle mounted slidably on the cap body for moving between an extended and enclosed position. A plastic injection device is disclosed in U.S. Pat. No. 2,677,373 which teaches a hypodermic injection device adapted to be furnished filled and sealed as sterile units until used. In U.S. Pat. No. 3,559,645 a disposable syringe containing a premeasured amount of medication in a hermetically sealed syringe is also provided.

A needle cap is disclosed in U.S. Pat. No. 5,242,421 having an elongated channel extending axially thereof to receive and hold a needle of a syringe by transverse movement therebetween. In U.S. Publication 2007/01138681, a cap for a medical device having two cap parts assemblable together to form a single integrated cap defining a gap therebetween into which an object may be inserted is disclosed.

A safety cap assembly for needles is disclosed in U.S. Pat. No. 5,807,352 which obviates the need for a medical professional to manually place the device in a position on the used syringe needle. In U.S. Pat. No. 5,125,415, a syringe tip cap with a self-sealing feature is taught for purging air from a syringe-like container. A filter allows air to pass therethrough; however, when liquid from the container is drawn through the filter, the filter expands and prevents further fluid flow therethrough.

The present device is not directly associated with the use or protection of needles of a hypodermic syringe, but rather with providing substantially greater convenience in the sterilization of needleless connections associated with assembly of IV components and tubing in a medical procedure setting and to replace the individually sealed sterilization swabs now required to effect sterilization of these needleless connections.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

This invention is directed to a sterilization cap carried on a needle support end of a syringe. The cap includes a main body having first and second ends divided by a separating bottom or wall extending transversely across a mid-portion of the main body. The first end connectable to the needle support end of the syringe, as well as being connectable onto a male adaptor end of an IV primary or extension line. A sponge secured within a sponge cavity defined between the second end opening and the bottom is saturated with a sterilizing liquid. A removable cover attached to the second end sealingly encloses the sponge within said sponge cavity until use. The second end is sized, when the cover is removed, to fit over the tip of a CLAVE needleless connector, on one end of an IV or IV extension tubing a distance sufficient to compress the sponge which sterilizes the needleless connector tip with sterilizing liquid expressed from the sponge.

It is therefore an object of this invention to replace the use of individually packaged sterilization swabs in a medical setting wherein a swab heretofore has been used to manually rub and sterilize needleless fittings associated with IV connectors and tubing in a medical setting.

It is another object of this invention to provide a syringe sterilization cap which is conveniently carried on the end of a prepackaged syringe which is sealed and ready for use in sterilizing needleless fittings and connectors used in conjunction with IV installations in a medical procedure setting.

Still another object of this invention is to provide a syringe sterilization cap which will conveniently sterilize all needleless connections associated with IV installation activity in a medical setting by either manually holding the cap during its use or maintaining it onto the end of the syringe for more convenient control and use.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWING(S)

Exemplary embodiments are illustrated in reference figures of the drawings. It is intended that the embodiments and figures disclosed herein are to be considered to be illustrative rather than limiting.

DETAILED DESCRIPTION OF THE INVENTION

Figure 1:
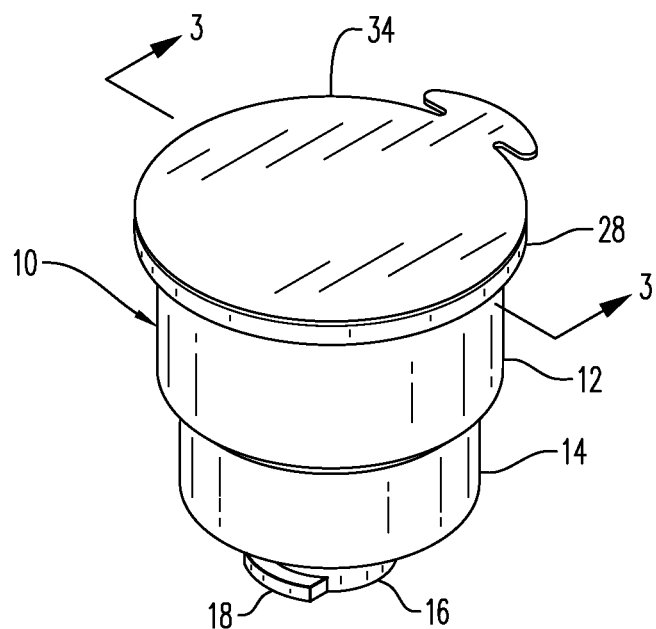
FIG. 1 is a perspective view of the invention 10.
Figure 2:
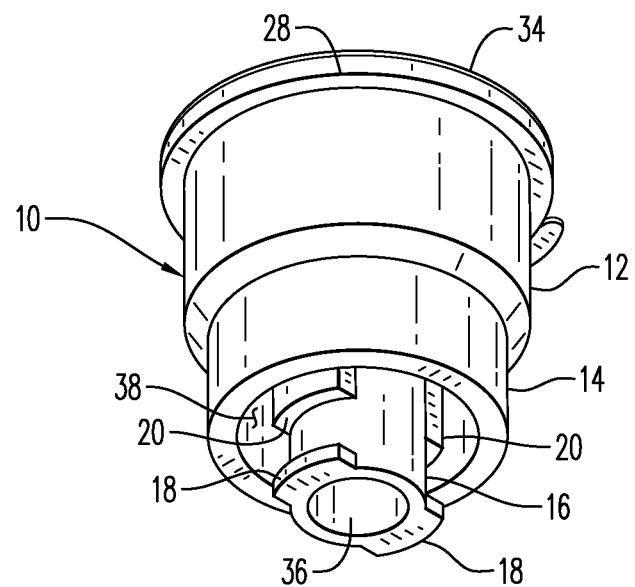
FIG. 2 is another perspective of the invention 10.
Figure 3:
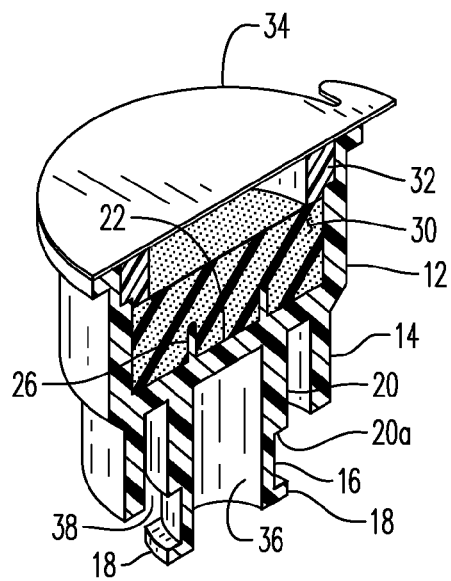
FIG. 3 is a perspective longitudinal section view of the invention 10.
Figure 4:
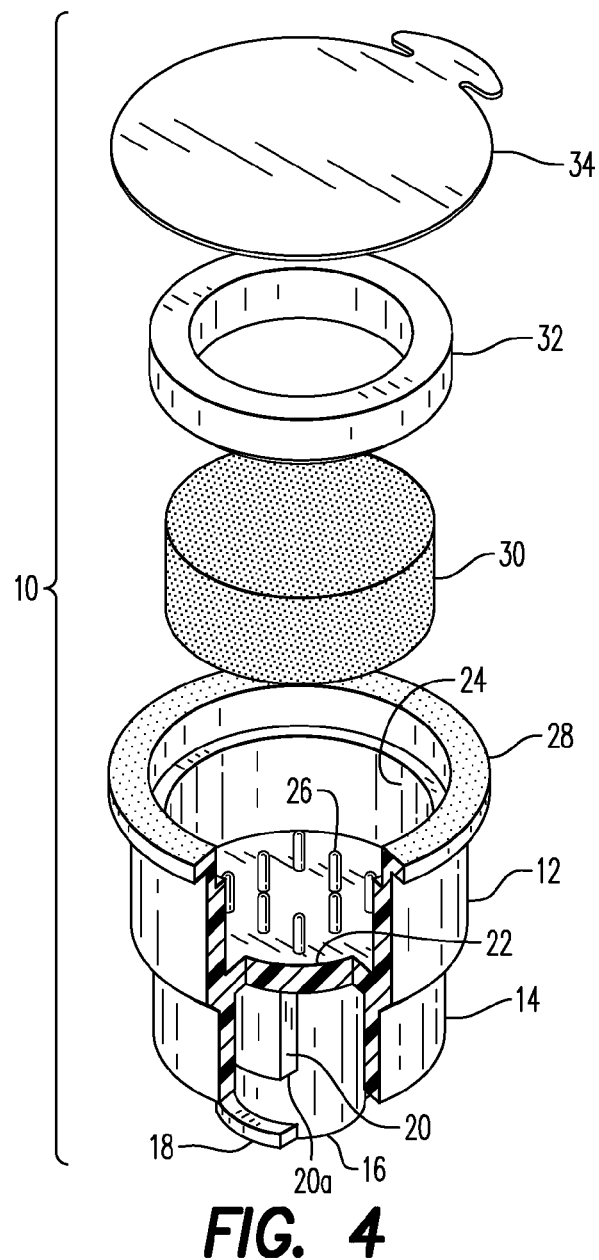
FIG. 4 is an exploded perspective view of the invention 10.

Nomenclature 10. sterilization cap
12. main body
14. barrel oversleeve
16. barrel inner sleeve
18. male locking lug
20. stop
22. bottom
24. sponge cavity
26. sponge retention prongs
28. flange
30. sterilizing liquid-saturated sponge
32. sponge retention ring
34. peel off cover
36. syringe receiving cavity
38. barrel clearance cavity Referring now to the drawings, and firstly to FIGS. 1 to 4, the invention is there shown generally at numeral 10 and includes a molded plastic main body 12, preferably formed of ABS plastic of any selected color or other suitable material. The main body 12 includes a reduced in diameter barrel oversleeve 14 forming a portion of a first end of the main body 12. A transverse bottom or wall 22 extending across a midportion of the main body 12 defines the proximal end of the barrel oversleeve 14. Extending from the bottom 22, a hollow cylindrical barrel inner sleeve 16 extends coaxially with, and beyond the end of the barrel oversleeve 14 and includes outwardly extending male locking lugs 18 formed thereon. Disposed on the outer surface of the barrel inner sleeve 16 are two opposed stops 20 having stop surfaces 20a thereof. A cylindrical barrel clearance cavity 38 best seen in FIG. 3 is defined between the inner surface of the barrel over sleeve 14 and the outer surface of the barrel inner sleeve 16.

The second end of the main body 12 is also cylindrical having a hollow sponge cavity 24 and an outwardly extending annular flange 28 defining the opening of the second end of the main body 12. A disc-shaped absorbent matrix or sponge 30 is sized to snugly fit within the sponge cavity 24 and is saturated with a sterilizing liquid such as isopropyl alcohol, BETADINE solution, or other suitable sterilizing liquid. The sterilizing liquid-saturated sponge 30 is stabilized from substantial movement, except for compression of the central portion thereof (as will be later described) by a plurality of spaced longitudinally extending prongs 26 connected to, or formed as a unit with, the bottom 22. These prongs 26 penetrate into the sponge 30 so as to prevent rotation of the sponge with respect to the sterilization cap 10 during use. Further, an annular-shaped sponge retention ring 32 is tightly fit into the opening of the second end of the body 12 and positioned inwardly of, and co-planar with, the flange 28.

To seal the sponge cavity 24 from air which would otherwise evaporate the sterilizing liquid within the sponge 30, a peel off cover 34 is adhesively attached to the surface of the flange 28, the cover 34 having a tab which facilitates the removal of the cover 34 when the sterilization cap 10 is ready for use.

Referring now to FIGS. 5, 6, 7, 8 and 11, the sterilization cap 10 is preferably provided connected to, and serving as a sealing cap for and covered a conventional hypodermic syringe. The syringe includes a threaded Luer Lock of a barrel having a central cylindrical needle support tube and female threads of the Luer Lock. This syringe structure facilitates the quick and easy installation or removal of a conventional end cap or a hypodermic needle.

Figure 5:
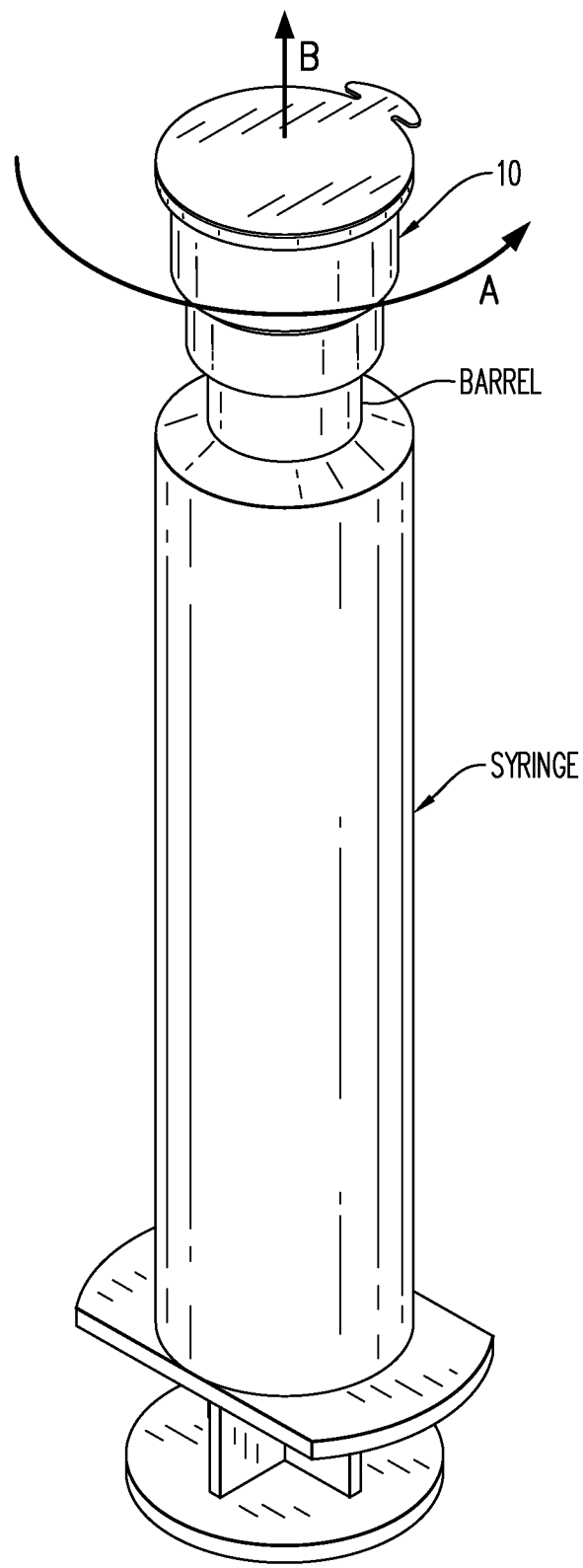
FIG. 5 is a perspective view of the invention 10 attached to a threaded leur lock of the barrel of a syringe.
Figure 6:
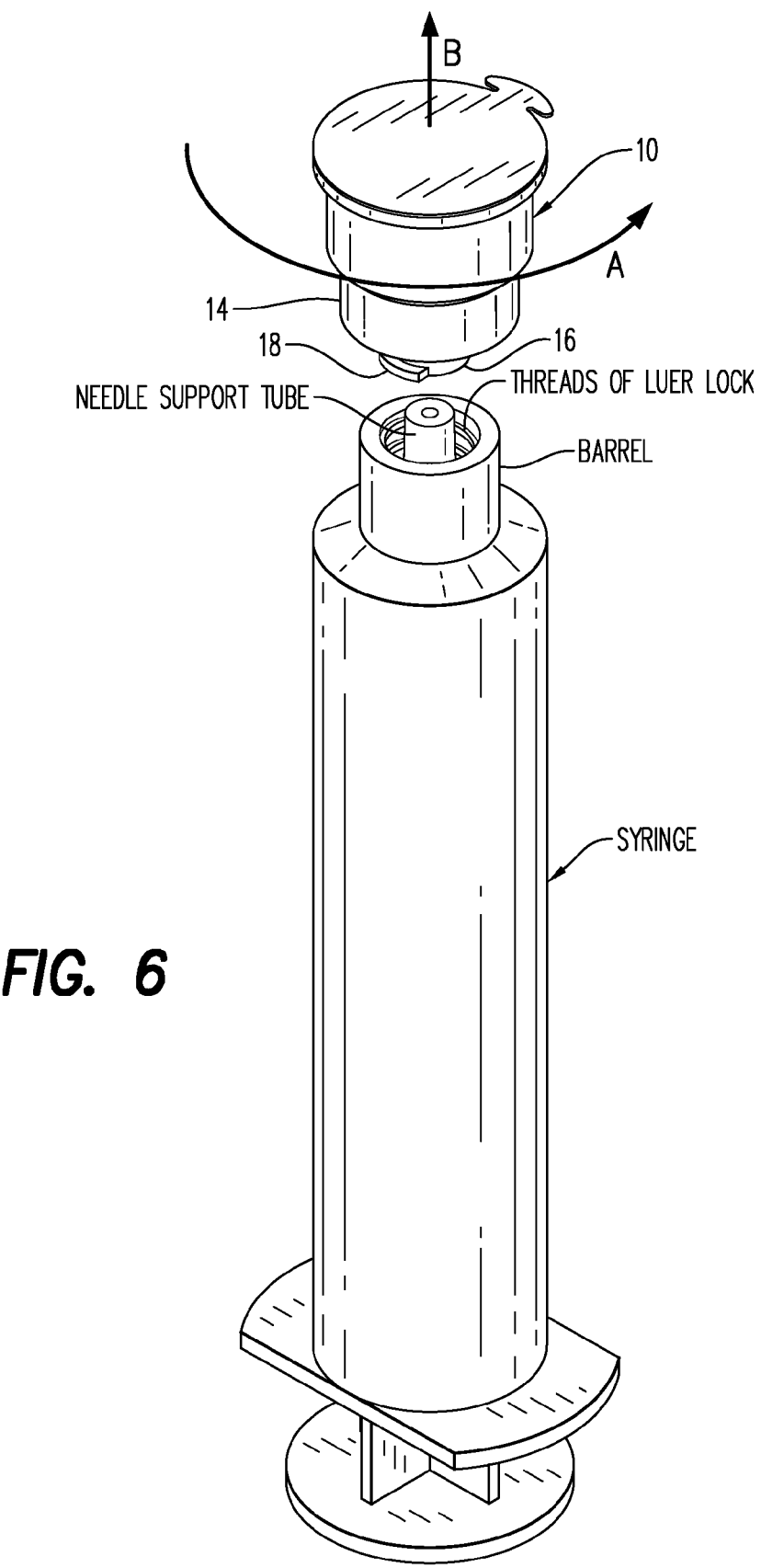
FIG. 6 is an exploded view of FIG. 5 showing the removal of the invention 10 from the syringe.

The syringe receiving cavity 36 is sized in diameter and length to snugly fit over and sealingly engage with the tapered needle support tube best seen in FIGS. 6, 11, 13, 15 and 16. The barrel clearance cavity 38 fits in close alignment over the cylindrical barrel and, when the sterilization cap 10 is positioned onto the syringe end as shown in FIG. 5 and rotated in the opposite direction of arrow A, the male locking lugs 18 threadably engage into the threads of the Luer Lock. To remove the sterilization cap 10, rotation in the direction of the arrow A showing in FIGS. 5 and 6 disengage the male locking lugs 18 from the Luer Lock threads, after which manual longitudinal force in the direction of arrow B disengages the barrel inner sleeve 16 from the needle support tube.

Figure 7:
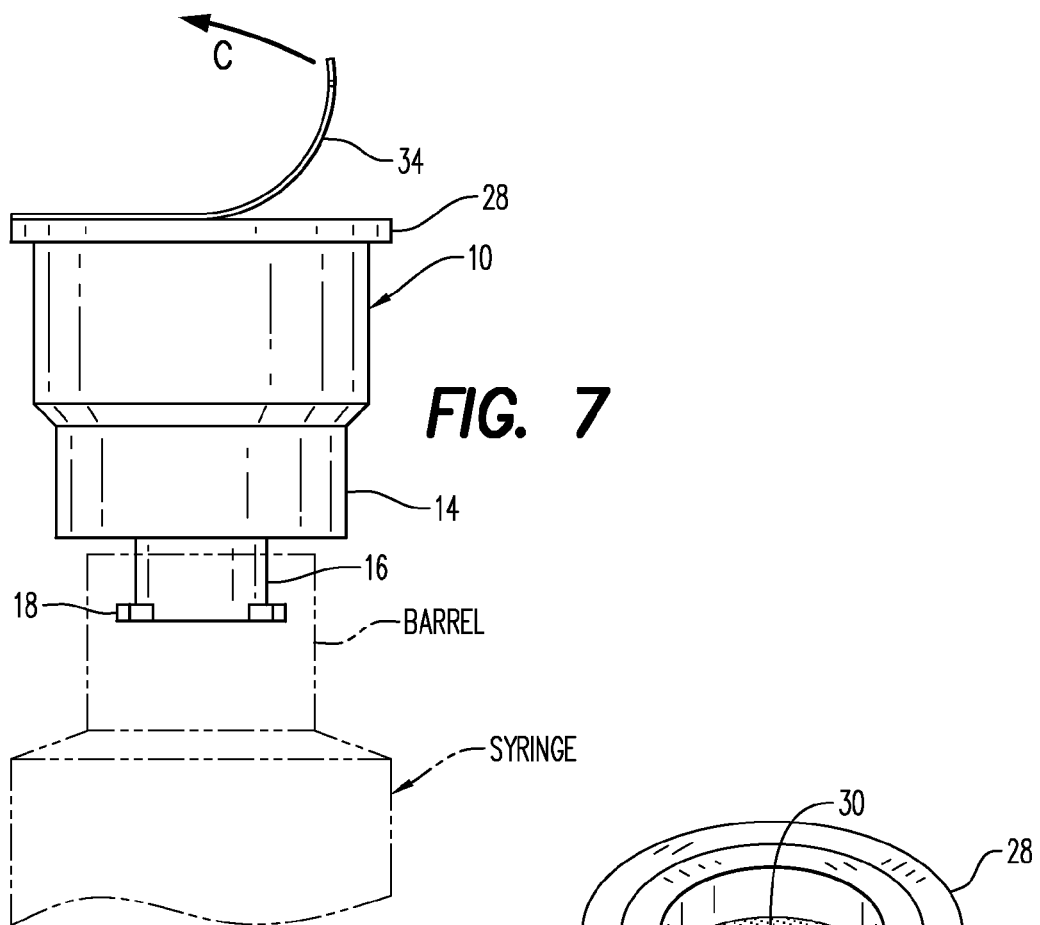
FIG. 7 is a side elevation view of the invention 10 showing removal of the protective cover, the syringe being shown in phantom for reference.
Figure 8:
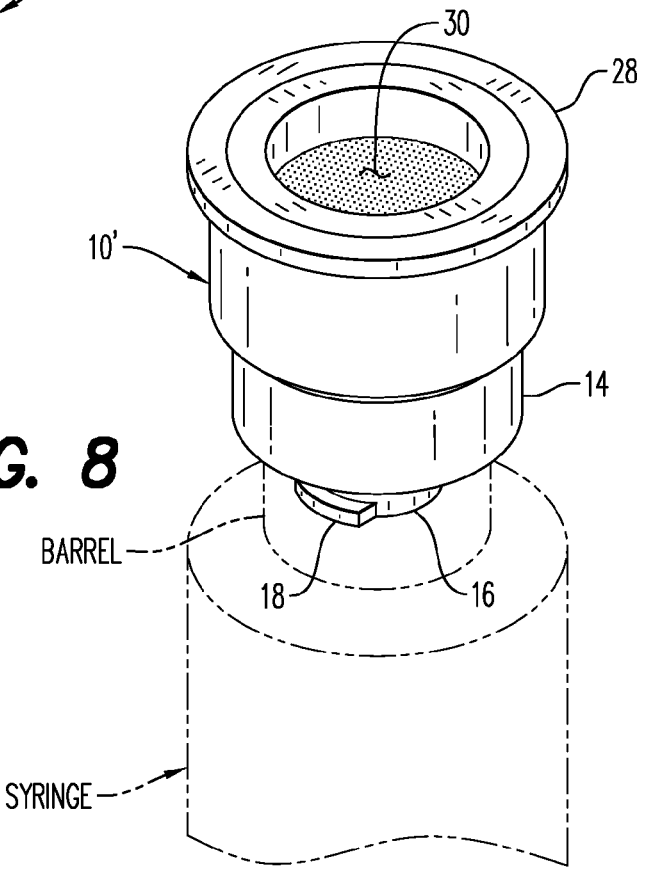
FIG. 8 is a perspective view of FIG. 7 showing the cover completely removed.
Figure 9A:
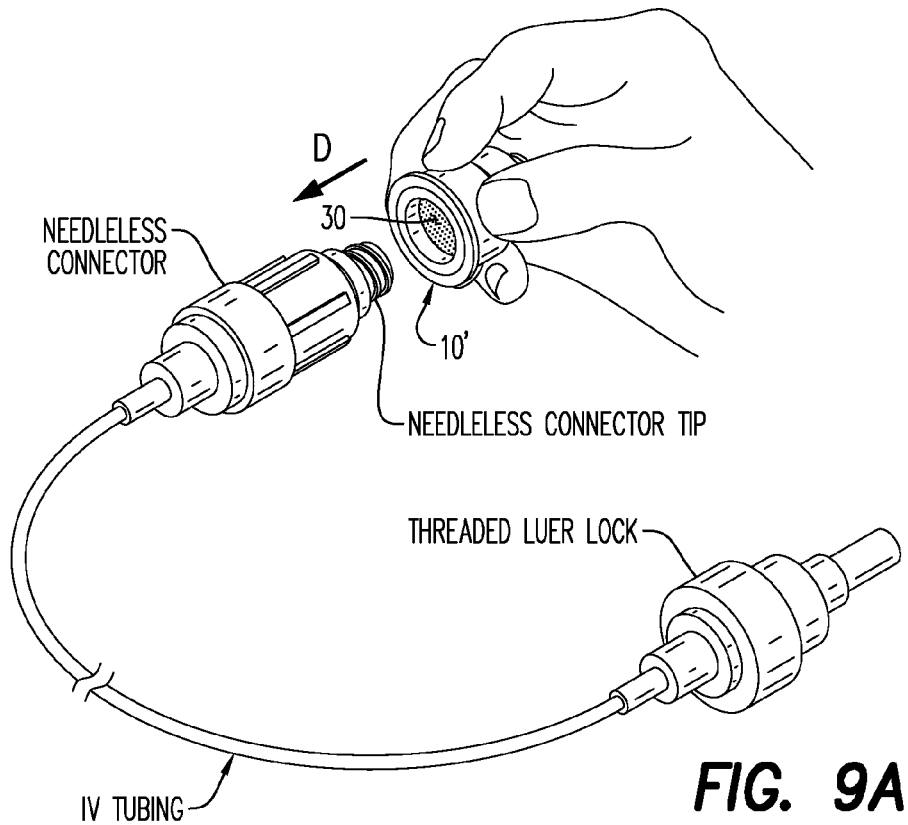
FIG. 9A is a perspective view showing the invention 10' with the protective cover removed and being hand-held and used manually to sterilize the CLAVE needleless connector tip of an IV tubing.
Figure 9B:
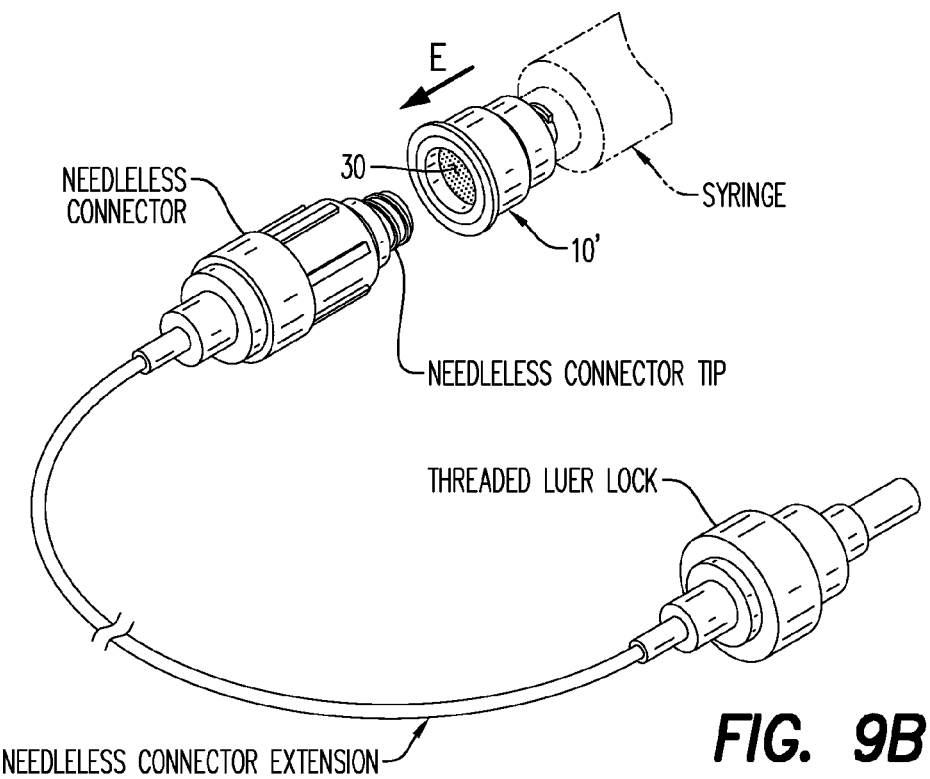
FIG. 9B is a view similar to FIG. 9A showing the invention 10' still attached to the syringe in an alternate use mode.
Figure 10:
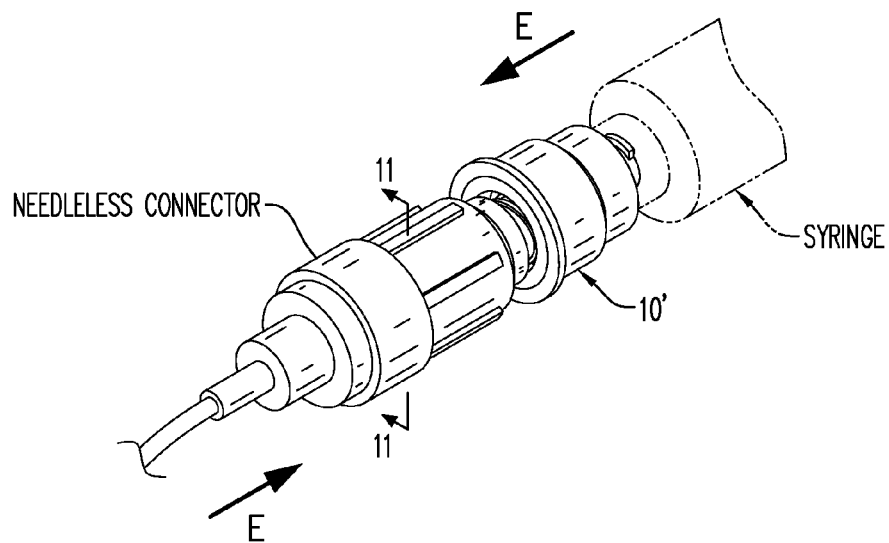
FIG. 10 is an enlarged view of a portion of FIG. 9B as the invention engages with the CLAVE needleless connector.
Figure 11:
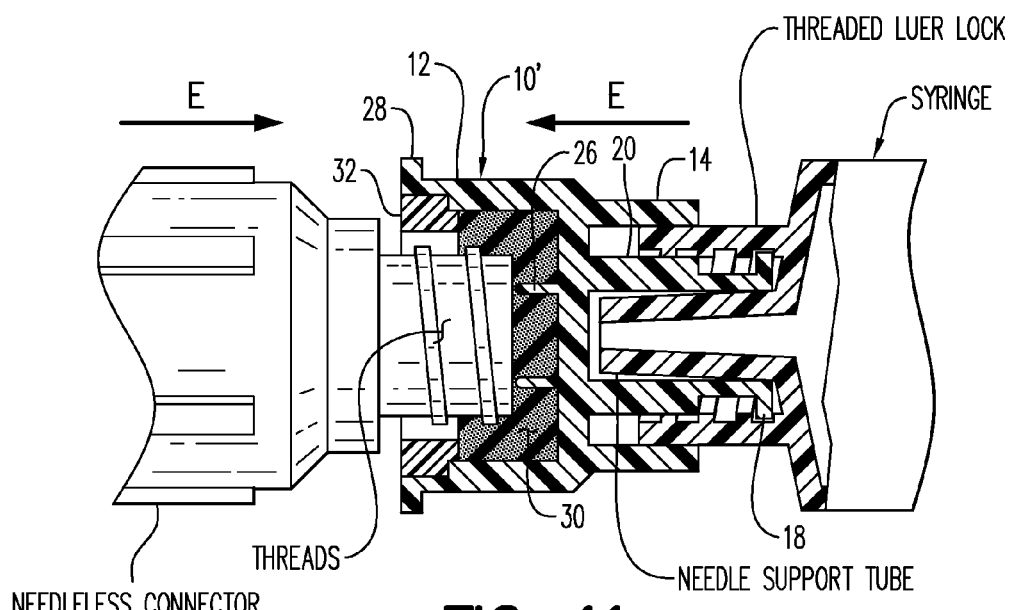
FIG. 11 is a section view in the direction of 11-11 in FIG. 10.
Figure 12:
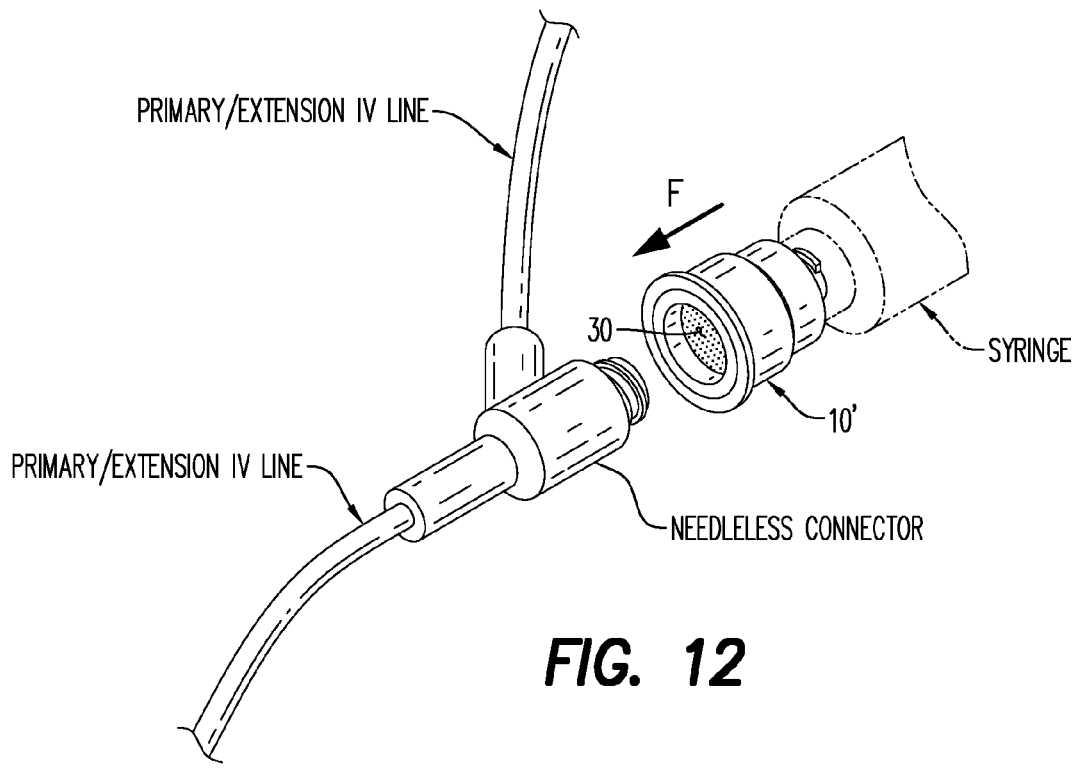
FIG. 12 is a perspective view of the invention 10 remaining attached to the syringe (shown in phantom) being used to sterilize the female needleless connector and of a primary or an IV extension line.

Once the cover 34 has been peeled away from the flange 28 in the direction of arrow C as seen in FIG. 7, the sterilization cap 10' may be used either while attached to the syringe as seen in FIGS. 9B, 10, 11, and 12, or manually held as seen in FIG. 9A. However, the purpose and utility of such alternate use is the same: to sterilize the tip of a CLAVE needleless connector of a typical IV tubing in preparation for interconnection of the CLAVE needleless connector tip to an IV needle. After the cover 34 has been removed, the open sterilization cap 10' may be used hand-held by forcing the sponge 30 in the direction of arrow D against the CLAVE needleless connector tip in FIG. 9A or in the direction of arrow E while remaining connected to the syringe as shown in FIGS. 9B, 10, 11 and 12. Both methods of use produce the same result: to express disinfecting liquid from the sponge 30 over the CLAVE needleless connector tip so as to fully sterilize the CLAVE needleless connector tip before being attached to an IV tubing with Luer Lock connection to a syringe with a Luer Lock end (including syringes prefilled with medications or saline solution) which can then be connected sterile.

Figure 13:
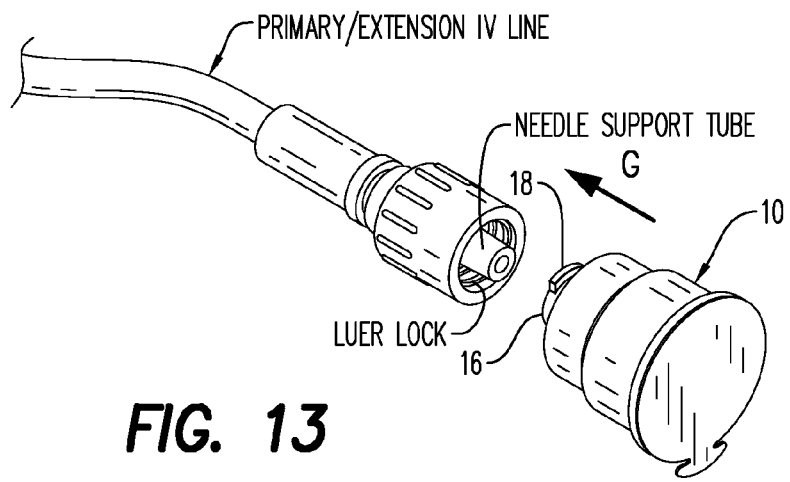
FIG. 13 is a perspective view of the invention 10 being temporarily attached to the needle support tube of a Luer Lock in preparation for subsequent sterilization use as previously described.
Figure 14:
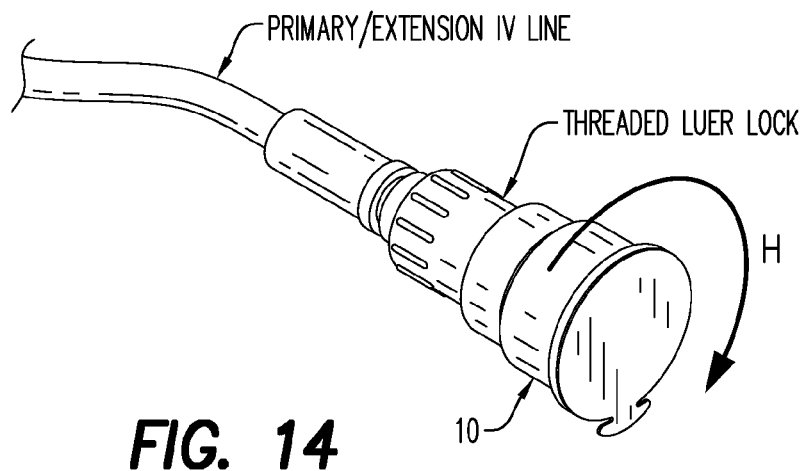
FIG. 14 is a perspective view showing the locking engagement of the invention 10 from FIG. 13.

Although the preferred embodiment of prepackaging the sterilization cap 10 attached to a syringe, the sterilization cap 10 may also be prepackaged with a primary or extension IV line as seen in FIGS. 13 to 16. In FIGS. 13 and 14, the first end of the sterilization cap 10 may be attached to a threaded leur lock male adapter in the direction of arrow G which engages the barrel inner sleeve 16 over the needle support tube. Thereafter, the sterilization cap 10 is rotated in the direction of arrow H in FIG. 14 to engage the male locking lugs 18 into the female threads of the Luer Lock as previously described.

Figure 15:
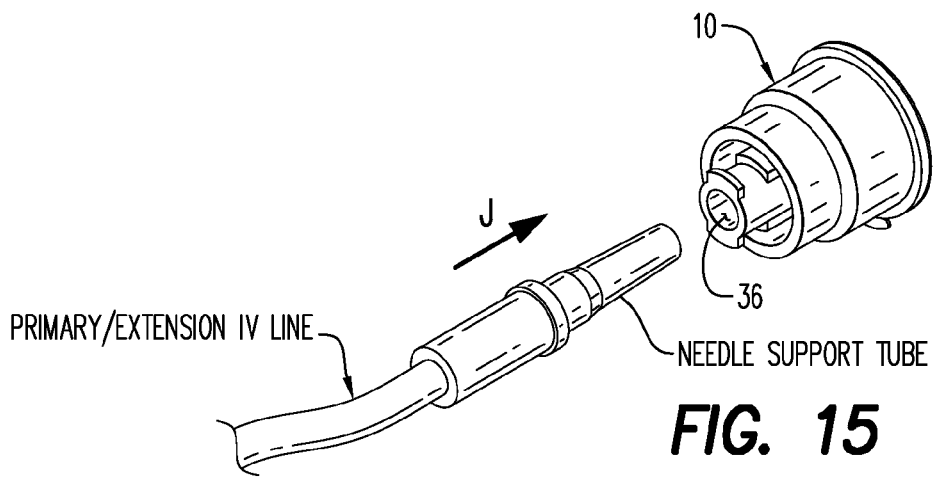
FIG. 15 is a perspective view showing the temporary engagement of the invention 10 onto a needle support tube without the Luer Lock.
Figure 16:
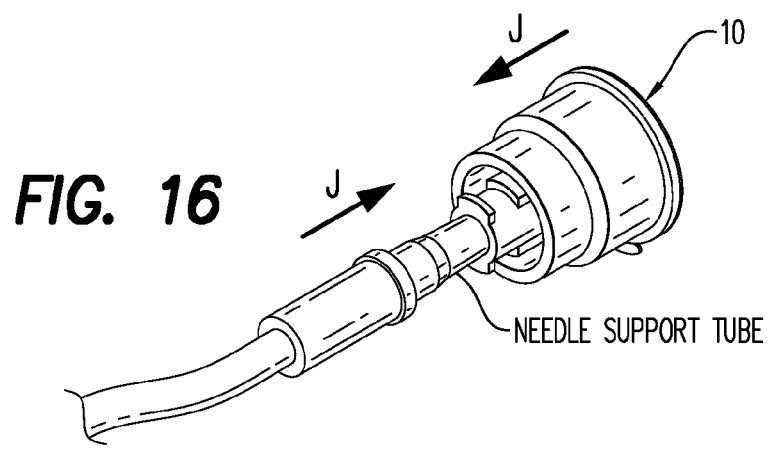
FIG. 16 is a perspective view similar to FIG. 15 showing the invention 10 attached onto the needle support tube.

Alternately as seen in FIGS. 15 and 16, the sterilization cap 10 may be releasibly engaged onto the tapered needle support tube without the accompanying Luer Lock of the primary or extension IV line by forcing the needle support tube into the syringe receiving cavity 36 in the direction of arrow J.

While a number of exemplary aspects and embodiments have been discussed above, those of skill in the art will recognize certain modifications, permutations and additions and subcombinations thereof. It is therefore intended that the following appended claims and claims hereinafter introduced are interpreted to include all such modifications, permutations, additions and subcombinations that are within their true spirit and scope.

The invention claimed is:

1. A sterilization cap carried on a needle support end of a syringe comprising:
   a main body having first and second ends thereof and a separating bottom extending across a mid-portion of said main body, said first end sealingly connectable to the needle support end, said first end also being sealingly connectable onto a male adaptor end of a primary or IV extension line:
   said first end including a cylindrical barrel clearance cavity defined between an inner surface of a barrel oversleeve and an outer surface of a barrel inner sleeve, an inner surface of said barrel inner sleeve being sealingly engageable with the needle support end:
   said second end of said main body defining a hollow sponge cavity and an outwardly extending annular flange defining an opening of said second end;
   a plurality of spaced longitudinally extending prongs coupling to said separating bottom for positioning within said sponge cavity;
   a sponge positioning within said sponge cavity and being saturated with a sterilizing liquid;
   said prongs penetrating into said sponge for preventing rotation of said sponge relative to said main body;
   an annular shaped sponge retention ring frictionally engaging with said opening of said second of said main body;
   said annular shaped sponge retention ring positioning inwardly of and co-planar with said outwardly extending annular flange for preventing removal of said sponge from said hollow sponge cavity;
   a removable cover attached to said second end to sealingly enclose said sponge within said sponge cavity; and
   said second end being sized, when said cover is removed, to fit over a needleless connector tip of an extension or IV tubing a distance sufficient to compress said sponge to sterilize said needleless connector with sterilizing liquid expressed from said sponge.

2. A sterilization cap sealingly engageable with a needle support end of a syringe as a cap, and, when being removed therefrom, sterilizingly engageable with components connectable to the syringe, comprising:
   a main body having first and second ends thereof and a separating bottom extending across a mid-portion of said main body, said first end sealingly connectable to the needle support end, said first end also being connectable onto a male adaptor end of a primary or IV extension line;
   said first end including a cylindrical barrel clearance cavity defined between an inner surface of a barrel oversleeve and an outer surface of a barrel inner sleeve, an inner surface of said barrel inner sleeve being sealingly connectable onto the needle support end to prevent leakage of medicine from the syringe;
   said second end of said main body defining a hollow sponge cavity and an outwardly extending annular flange defining an opening of said second end;
   a plurality of spaced longitudinally extending prongs coupling to said separating bottom for positioning within said sponge cavity;
   a sponge positioning within said sponge cavity and being saturated with a sterilizing liquid;
   said prongs penetrating into said sponge for preventing rotation of said sponge relative to said main body;
   an annular shaped sponge retention ring frictionally engaging with said opening of said second end of said main body,
   said annular shaped sponge retention ring positioning inwardly of and co-planar with said outwardly extending annular flange for preventing removal of said sponge from said hollow sponge cavity;
   a removable cover attached to said second end to sealingly enclose said sponge within said sponge cavity; and
   said second end being sized, when said cover is removed, to fit over a needleless tip of an extension or IV tubing a distance sufficient to compress said sponge to sterilize said needleless tip with sterilizing liquid expressed from said sponge.

3. A multifunction sterilization cap sealingly carried on a needle support end of a syringe comprising:
   a main body having first and second ends thereof and a separating bottom extending across a mid-portion of said main body;
   said first end including a syringe receiving cavity sealingly securable onto a needle support tube of the needle support end, said first end also including male locking lugs which releasably lockingly engage with female threads of a barrel of the syringe, said first end also being sealingly connectable onto a male adaptor end of a primary or IV extension line;

said second end of said main body defining a hollow sponge cavity and an outwardly extending annular flange defining an opening of said second end;

a plurality of spaced longitudinally extending prongs coupling to said separating bottom for positioning within said sponge cavity;

a sponge positioning within said sponge cavity and being saturated with a sterilizing liquid;

said prongs penetrating into said sponge for preventing rotation of said sponge relative to said main body;

an annular shaped sponge retention ring frictionally engaging with said opening of said second end of said main body;

said annular shaped sponge retention ring positioning inwardly of and co-planar with said outwardly extending annular flange for preventing removal of said sponge from said hollow sponge cavity;

a removable cover attached to said second end to sealingly enclose said sponge within said sponge cavity; and said second end being sized, when said cover is removed, to fit over a needleless tip of an extension or IV tubing a distance sufficient to compress said sponge to sterilize said needleless tip with sterilizing liquid expressed from said sponge.

* * * * *